US012601019B2

(12) United States Patent
Liu et al.

(10) Patent No.: US 12,601,019 B2
(45) Date of Patent: Apr. 14, 2026

(54) AUTOMATIC PATHOGEN-FROM-EXPIRATION DETECTION SYSTEM AND METHOD

(71) Applicant: NANJING ORIGINALCODE PARTNERSHIP (LIMITED PARTNERSHIP), Nanjing (CN)

(72) Inventors: Quanjun Liu, Nanjing (CN); Xiaoxiang Zhou, Nanjing (CN); Zhanping Li, Nanjing (CN); Zhen Zhang, Nanjing (CN); Xiaoming Han, Nanjing (CN); Ying Xu, Nanjing (CN); Yan Huang, Nanjing (CN); Zuhong Lu, Nanjing (CN)

(73) Assignee: NANJING ORIGINALCODE PARTNERSHIP (LIMITED PARTNERSHIP), Nanjing (CN)

( * ) Notice: Subject to any disclaimer, the term of this patent is extended or adjusted under 35 U.S.C. 154(b) by 622 days.

(21) Appl. No.: 18/016,056

(22) PCT Filed: Aug. 6, 2021

(86) PCT No.: PCT/CN2021/111094
§ 371 (c)(1),
(2) Date: Jan. 13, 2023

(87) PCT Pub. No.: WO2022/033394
PCT Pub. Date: Feb. 17, 2022

(65) Prior Publication Data
US 2023/0287522 A1    Sep. 14, 2023

(30) Foreign Application Priority Data
Aug. 14, 2020    (CN) .......................... 202010821390.4

(51) Int. Cl.
*C12Q 1/70* (2006.01)
*B01L 3/00* (2006.01)
(Continued)

(52) U.S. Cl.
CPC ........ *C12Q 1/701* (2013.01); *B01L 3/502761* (2013.01); *C12Q 1/6851* (2013.01);
(Continued)

(58) Field of Classification Search
CPC ......... B01L 2200/0647; B01L 2200/16; B01L 2300/0645; B01L 2300/0883;
(Continued)

(56) References Cited

U.S. PATENT DOCUMENTS

2018/0099278 A1*   4/2018  Niemeyer ............. F04B 19/006

FOREIGN PATENT DOCUMENTS

CN        111013674 A      4/2020
CN        111912697 A     11/2020
CN        112226360 A      1/2021

* cited by examiner

*Primary Examiner* — Gurpreet Kaur
(74) *Attorney, Agent, or Firm* — MUNCY, GEISSLER, OLDS & LOWE, P.C.

(57) ABSTRACT

An automatic pathogen-from-expiration detection system includes a gas pathogen recovery unit, a pathogen concentration unit and a sample detection unit. The method includes making the sample recovered by the gas pathogen recovery unit enter the pathogen concentration unit; in the pathogen concentration unit, gradually biasing the pathogen particles in the sample to the positive electrode side into the concentration channel under the action of the electrode; applying a fluctuating voltage greater than zero to a single sub-positive electrode, and alternating the voltage of the sub-positive electrode adjacent thereto with the fluctuating voltage, so that a varying potential difference is formed between the adjacent sub-positive electrodes, wherein the
(Continued)

pathogen particles are gradually enriched in the middle region of the two adjacent sub-positive electrodes, and the concentrated sample is driven to move to the sample detection unit; and immediately detecting the concentrated sample in the sample detection unit.

11 Claims, 3 Drawing Sheets

(51) Int. Cl.
*C12Q 1/6851* (2018.01)
*G01N 1/40* (2006.01)

(52) U.S. Cl.
CPC ........ *G01N 1/40* (2013.01); *B01L 2200/0647* (2013.01); *B01L 2200/16* (2013.01); *B01L 2300/0645* (2013.01); *B01L 2300/0883* (2013.01); *G01N 2001/4038* (2013.01)

(58) Field of Classification Search
CPC ......... B01L 3/502761; B01L 3/502784; C12Q 1/6851; C12Q 1/701; G01N 1/2273; G01N 1/40; G01N 2001/2244; G01N 2001/2282; G01N 2001/4038
See application file for complete search history.

AUTOMATIC PATHOGEN-FROM-EXPIRATION DETECTION SYSTEM AND METHOD

TECHNICAL FIELD

The present invention belongs to the field of respiratory tract pathogen detection technology, in particular to a system and method for continuous and uninterrupted real-time detection of respiratory tract viruses based on microfluidic chips.

BACKGROUND ART

Respiratory tract infectious diseases often outbreak, in the past decade, there have been Corona Virus Disease 2019, SARS, Middle East respiratory syndrome, avian, etc. Without effective control, infectious diseases will cause a virus pandemic, which poses a great threat to human health and social economy. The respiratory tract virus invades the respiratory tract as a portal entry, proliferates in the mucosal epithelial cells of the respiratory tract, and causes local respiratory tract infection or lesions of tissues and organs outside the respiratory tract. It is mostly ssRNA virus, enveloped and spike, mainly transmitted through the respiratory tract, and the virus is located in the respiratory tract. Recurrent infection with high prevalence.

The major solution for prevention and control of infectious diseases can be that the preventive measures of infectious diseases can be divided into three aspects: controlling the source of infection, cutting off the route of transmission and protecting susceptible population. One of the most important is the identification of the source of infection. Especially in highly populated areas such as subways, railway stations and airports, the possibility of outbreaks of infectious diseases can be reduced very effectively if the source of infection can be detected and isolated in a timely manner. Therefore, it would be desirable to develop a system for continuous and uninterrupted real-time detection of respiratory viruses to enable monitoring of potential sources of infection in areas where there are mobile populations all around.

Respiratory diagnosis, as a non-invasive diagnostic method with good prospects, has been paid more and more attention. Breathing diagnosis is characterized by being nondestructive and cheap, and the research on its diagnosis mainly focuses on two types of markers: volatile organic compounds in the exhaled gas and biomarkers in the exhaled gas condensate.

Thousands of volatile organic compounds are present in human exhaled gas, most of concentration is at picomolar and lower levels, and only a small fraction of which are disease-related. The exhaled gas is condensed by a cooling device to obtain a condensate. Condensate is also a nondestructive and convenient way to obtain human health information. The biomarkers collected by the condensate contain a very large variety of ions, metabolites, and molecules such as nucleic acids, ATP, ammonia, hydrogen peroxide, prostaglandins, lactic acid, nitrogen oxides, peptides, and cytokines, in addition to water, which accounts for approximately 99% of the total volume. Thus, viral carriers can be found by detecting biomarkers such as RNA of respiratory viruses in the breath condensate.

Traditionally, the detection of virus in gas includes sampling and detection. There are four main methods for collecting microorganisms in gas, which are gravity sampling, inertial impaction, filtration retention and electrostatic deposition. The main idea is to use an air sampler to transfer microorganisms in the air to a certain medium, which may be liquid, solid or semi-solid. Since fewer viruses are collected, it is necessary to culture the viruses first and then detect them by sequencing, chemiluminescence or optical means.

According to the gravity sampling method, under the action of the gravity of microbial aerosol, microbial particles are collected in the culture dish within a certain period of time, and then cultured and grown into colonies at appropriate temperature for biological observation and study. The inertial sampling method is to use an air extraction pump to extract air containing microbial particles, and force the air to pass through a nozzle on a sampler to form a high-speed jet air stream; when leaving the nozzle, the jet air stream is forced to deflect, and particles with a particle size greater than or equal to the cutting particle size D50 (the aerodynamic diameter of particles when the collection efficiency is 50%, μm) are collected on the sampling medium due to the inertial effect; particles smaller than D50 escape with the deflection of the airflow due to the small inertia. An electrostatic sampler operates when charged particles enter an electric field, deflected by the force of the electric field, and therefore are collected on a polar plate.

However, these methods have certain drawbacks. The gravity sampling method has very low sampling efficiency for small particle size and small number of pathogens in the air, and is greatly affected by the airflow. The inertial sampling method is also not good for collecting germ particles with small particle size, and it is easy to damage microorganisms due to air jet during sampling operation. The filter-type sampler can reside germ particles on the filter material to collect the particles, however, if the sampling is continued for a long time, the microorganisms on the filter membrane are dehydrated to lose their activity. The electrostatic sampler has simple structure, small pressure drop, a large amount of air that can be collected, a high concentration ratio, a high efficiency of trapping fine particles, and can better maintain microbial morphology and biological activity. However, long sampling times, evaporation of media such as agar, droplets, etc. can cause changes in humidity within the sampler to affect collection efficiency.

For microbial analysis, at present, most of the microorganisms are detected by separation culture combined with microscopic observation, which is not only time-consuming (generally takes several days to several weeks), but also different microorganisms have different requirements for nutrients, so most microorganisms are difficult to culture rapidly by artificial means. The biological characteristics of some microorganisms determine that this species is not easy to multiply in large numbers in a short period of time, the types of microorganisms that can be analyzed by artificial culture are limited.

Microorganism analysis by means of molecular biology has become the focus of current research, mainly including the detection of virus nucleic acids and their specific proteins or glycopeptides. Among them, sequencing is the most accurate detection method for determining respiratory virus.

Detection of infectious viruses requires a good environment, skilled operators, and automation is the best way to solve this problem. It has become very important in crowd-intensive areas to develop a means and method for identifying the source of infection that can be directly processed, used, reduced links, directly processed, and unattended during processing.

In order to achieve continuous and uninterrupted real-time monitoring of the virus content in the air in the field, a complete process from sampling to detection needs to be completed, involving a large number of experimental equipment, while microfluidic laboratories provide a solution method. Microfluidic chip, also called Lab-on-Chip, is a technical platform that integrates basic operation units involved in chemical and biological fields, such as sample preparation, reaction, separation, detection and cell culture, sorting, lysis, enrichment, and detection, onto a chip of several square centimeters or less, and forms a network by microchannels, to control fluid to penetrate the whole system, to replace various functions of conventional chemical or biological laboratories. Microfluidic chips have been used by researchers to detect bacteria, viruses (HIV and syphilis), microorganisms, parasites, etc. in some environments. The characteristics of characterized by low cost, high efficiency, simple, easy integration, high degree of automation, good controllability, and good compatibility. Common microfluidic detection techniques include fluorescence detection, ultraviolet absorbance detection, chemiluminescence detection, electrochemical detection, mass spectrometry detection, biosensor detection, etc. Digital droplet analysis is a high-precision quantitative analysis method developed recently. The principle of digital droplet analysis is to use droplet technology to randomly distribute the target to be tested into a large number of droplets isolated from each other, each droplet is equivalent to an independent microreactor; positive and negative droplets are then distinguished against a direct or indirect signal of the target to be detected in the microdroplet. Positive droplets are read as 1, negative droplets are read as 0, and absolute quantitative analysis of the target to be detected can be achieved according to Poisson distribution algorithm. Compared with traditional analytical techniques, the most prominent feature of digital droplet analysis is that it has an absolute quantitative analysis capability independent of the standard. In addition, the digital analysis based on large-scale droplet dispersion system is significantly superior to the traditional quantitative analysis methods in terms of detection sensitivity and quantitative analysis accuracy. Since microfluidic technology is a useful tool for large-scale droplet manipulation, microfluidic chips have become the main platform for digital droplet analysis.

Digital droplet analysis does not rely on the absolute quantitative analysis capability of the standard and its advantages in sensitivity and accuracy of quantitative analysis, which is very beneficial for rapid virus detection in the field. However, the application of this technology in this field is rarely reported. The main reason for this is that droplet generation on microfluidic chips relies heavily on fluid-driving devices based on gas pressure or syringe pumps. In addition, if on-site detection is required, a corresponding fluorescence detection platform is also required, this type device is bulky and complicated to operate, and thus difficult to apply to on-site rapid detection. It would therefore be desirable to further integrate a correlation system to enable an uninterrupted, rapid and continuous sampling detection from sampling to detection based on a microfluidic platform to enable identification of potential sources of infection in dense areas.

In general, the existing pathogen detection techniques have certain limitations:

1) the sample processing and detection process is complex and time-consuming, requiring the coordination of multiple instruments;

2) the detection accuracy is low and false negative is high;

3) qualitative detection is a significant method to distinguish subtype and similar symptoms of influenza virus, resulting in cross-infection;

4) samples collected on site need to be packaged and sent to hospital for testing, lacking equipment that can be tested on site. In order to achieve timely and accurate isolation and treatment, and more effectively control the spread of the epidemic, there is an urgent need for a convenient and accurate on-site real-time pathogen detection technology.

SUMMARY OF THE INVENTION

It is an object of the present invention to provide an automated pathogen collection and detection system and method that enables continuous and rapid detection of respiratory viruses in human populations. The system first collects the exhaled gas, and then further concentrates the exhaled virus to obtain a concentrated solution. Combined with relevant detection devices, the system can achieve an integrated and automated continuous and rapid collection, concentration, and detection of pathogens. In order to solve the above technical problem, the present invention provides the following technical solutions:

the present invention firstly provides an automatic pathogen-from-expiration detection system, which comprises a gas pathogen recovery unit, a pathogen concentration unit, and a sample detection unit;

the gas pathogen recovery unit and the pathogen concentration unit are coupled to realize continuous loading and continuous detection;

the pathogen concentration unit comprises a microchannel, an electrode, and a filter element; the microchannel comprises a concentration channel and a sample channel; a filter element is provided between the concentration channel and the sample channel; the electrode comprises a positive electrode and a negative electrode, the positive electrode comprises several sub-positive electrodes provided in a spaced array on one side close to the concentration channel, and the negative electrode is provided on one side close to the sample channel; during the concentration, a fluctuating voltage greater than zero is applied to a single sub-positive electrode, and the voltage of the sub-positive electrode adjacent thereto alternates with the fluctuating voltage, so that a varying potential difference is formed between the adjacent sub-positive electrodes; the sample formed in the gas pathogen recovery unit flows into the microchannel, and under the action of the electrode, the pathogens in the sample are regionally enriched on the positive electrode side of the concentration channel to form a concentrated sample in the concentration channel; and the sample detection unit is connected to the concentration channel for detecting pathogens in the concentrated sample.

Still further, a first driving device is included, and the sample is driven into the microchannel by the first driving device.

Further, the first driving device comprises a positive pressure pump, and/or a negative pressure pump, and/or a syringe pump, and/or a peristaltic pump.

Further, the outlet and the inlet of the microchannel are provided with a pair of driving electrodes.

Further, the sample detection unit comprises a microfluidic channel, a temperature control module, a detection device, an oil storage device and a second driving device, inlets of the microfluidic channel are respectively in communication with the concentration channel and the oil storage device, the oil in the oil storage device is driven by the second driving device to form a water-in-oil droplet sample together with the concentrated sample at the inlet of the microfluidic channel, the temperature control module comprises several temperature control monomers to generate a required temperature change in the main region of the microfluidic channel, the water-in-oil droplet sample is amplified, and the amplified pathogen is detected by the detection device.

Further, the fluctuation form of the fluctuating voltage larger than zero comprises rectangular wave, and/or triangular wave, and/or sine wave.

Still further, the filter element is a semi-permeable membrane, and/or an array of micro-columns, and/or a gel polymer, and is a filter structure with voids.

Still further, the concentration channel has a width of less than that of the sample channel.

Further, the width $L_1$ of the sample channel and the width $L_2$ of the concentration channel satisfy:

$$L_1V_1/L_2V_2 \geq X$$

wherein $V_1$ is a flow rate of the sample channel, $V_2$ is a flow rate of the concentration channel, and X is a ratio of the concentration of the concentrated sample to the concentration of the sample before concentration.

The present invention also provides an automatic pathogen-from-expiration detection method, which comprises:

making the sample recovered by the gas pathogen recovery unit enter the pathogen concentration unit;

under the action of the positive electrode and the negative electrode, gradually biasing the pathogen particles to one side of the positive electrode, and making the pathogen particles enter the concentration channel through the filter element; applying a fluctuating voltage greater than zero on a single sub-positive electrode, wherein the voltage of the sub-positive electrode adjacent thereto alternates with the fluctuating voltage, forming a varying potential difference between the adjacent sub-positive electrodes, and the pathogen particles reciprocate between the two adjacent sub-positive electrodes and gradually enrich in the middle region of the two adjacent sub-positive electrodes; and driving the concentrated sample to move to the sample detection unit; and immediately detecting the concentrated sample in the sample detection unit.

Further, several sub-positive electrodes are provided, wherein some or all the single sub-positive electrodes are applied with a fluctuating voltage, and a fluctuating electric field is formed among a number of sub-positive electrodes therein, forming one or more enrichment regions, and the number of electrodes supplying voltage during enrichment can also be gradually reduced to form fewer enrichment regions for further enrichment.

The present invention has the following advantageous effects compared to the prior art:

with the automatic pathogen-from-expiration detection system of the present invention, it is possible to realize the continuous and rapid collection, concentration, and detection of pathogens, which is an automated and integrated rapid detection system for pathogens. The sample collection, concentration and detection are integrated, the detection time is short, the detection sensitivity is high, the consumption and low cost, and can realize continuous sampling and detection. The pathogen concentration unit greatly improves the sample concentration efficiency through accurate electrical control. The requirements of the experimental site are greatly reduced, and the on-site detection of public environment is realized. On the other hand, the present invention does not require professional handling of the sample, reducing professional dependence during use. Further, the sample is inactivated from the start of collection, eliminating the risk of secondary infection of the sample. Compared with the traditional pathogen detection scheme, the present invention realizes rapid detection for a large number of people, achieves high integration of highly sensitive detection technology for pathogens, and can be used for rapid and safe detection of pathogens in relatively concentrated places of people such as airports, stations, companies, etc.

Figure 1:
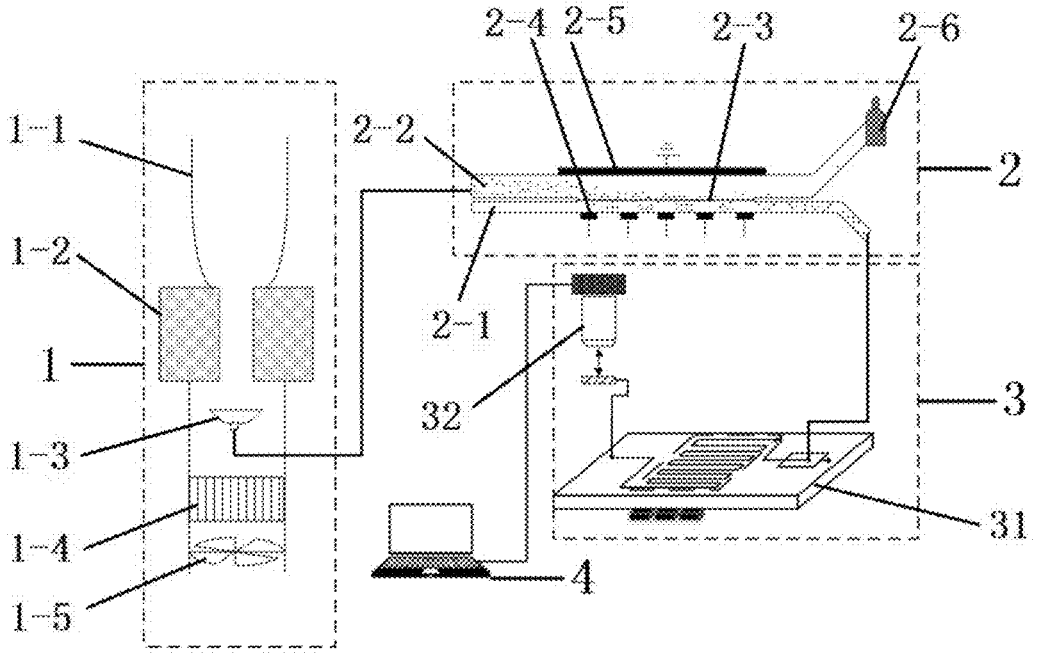
FIG. 1 is a schematic diagram of the structure of the automatic pathogen-from-expiration monitoring system in the embodiment.

Reference numerals: 1, pathogen recovery unit; 1-1, gas inlet; 1-2, cooling module; 1-3, collector; 1-4, filter; 1-5, fans; 2, pathogen concentration unit; 2-1, concentration channel; 2-2, sample channel; 2-3, filter element; 2-4, positive electrode; 2-5, negative electrode; 2-6, waste reservoir; 3, sample detection unit; 31, microfluidic amplification module; 31-1, droplet generation position; 31-2, microfluidic channel; 31-3, chip-type fluorescence detection position; 31-4, off-chip capillary fluorescence detection position; 31-5, temperature control module; 32, fluorescence detection module; 4, computer.

DETAILED DESCRIPTION OF THE INVENTION

Reference will now be made in detail to the embodiments of the present invention, examples of which are illustrated in the accompanying drawings, wherein like reference numerals refer to the same or similar elements throughout the several views, and wherein like reference numerals refer to the same or similar elements throughout the several views. The embodiments described below with reference to the figures are exemplary and are intended to be illustrative of the invention and are not to be construed as limiting the invention.

In the description of the embodiments, it should be noted that the terms "central", "upper", "lower", "left", "right", "vertical", "horizontal", "inner", "outer", and the like designate orientations or positional relationships based on the orientation or positional relationships shown in the drawings, are merely for convenience in describing the invention and to simplify the description, and do not indicate or imply that the referenced devices or elements must have a particular orientation, be constructed and operated in a particular orientation, and thus should not be construed as limiting the invention. Further, the terms "first", "second", and "third" are used for descriptive purposes only and are not to be construed as indicating or implying relative importance or implicitly indicating the number of technical features indicated. This embodiment provides an automatic pathogen-from-expiration detection system as shown in FIG. 1. The automatic pathogen-from-expiration detection system comprises a gas pathogen recovery unit 1, a pathogen concentration unit 2 and a sample detection unit 3.

Figure 3:
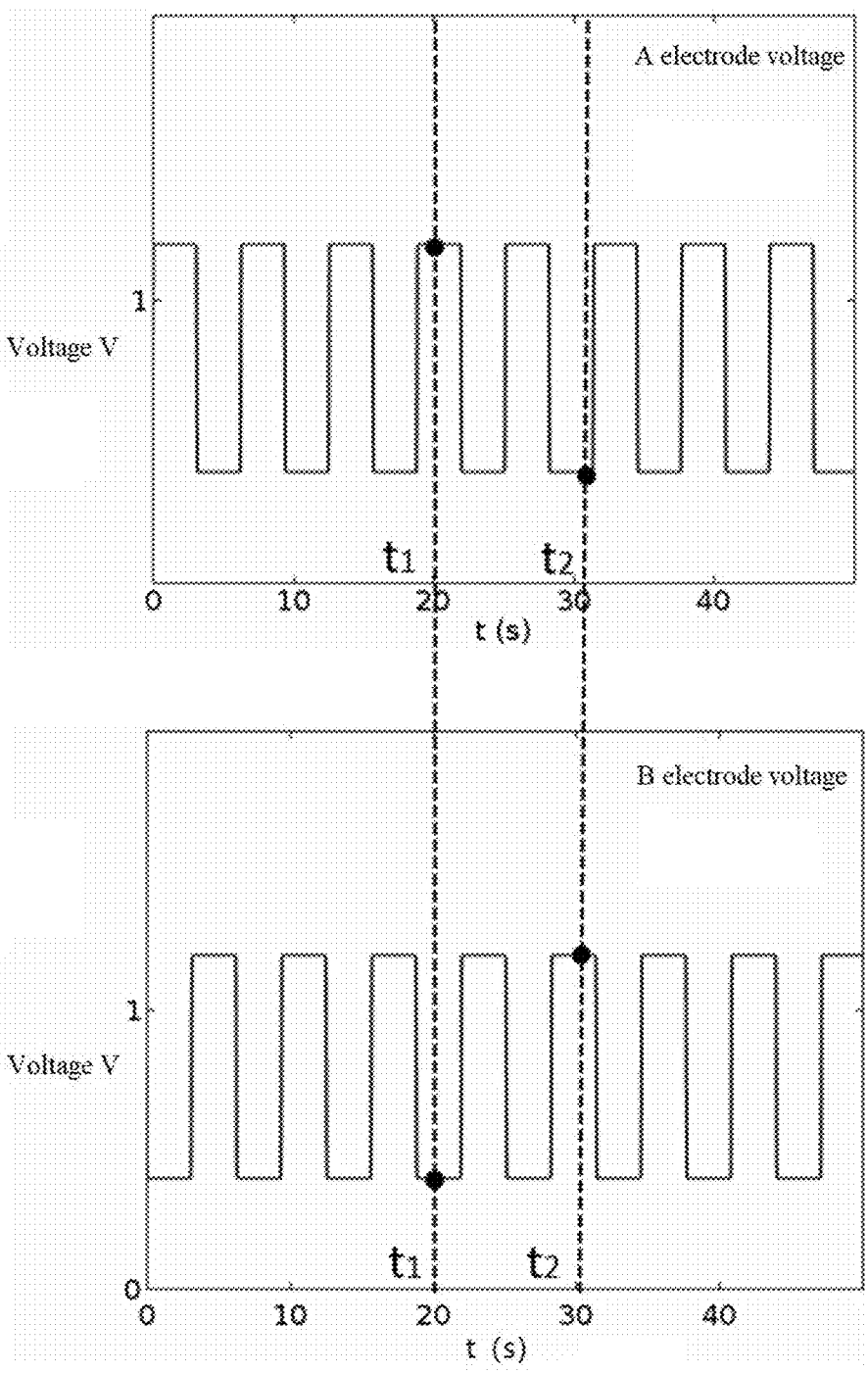
FIG. 3 is a schematic diagram showing voltages applied to a group of adjacent sub-positive electrodes (sub-positive electrode A, sub-positive electrode B) in an embodiment.

The gas pathogen recovery unit 1 is coupled with the pathogen concentration unit 2, the specific structure and form of the gas pathogen recovery unit 1 are not limited in the present invention, and any device capable of coupling with the pathogen concentration unit 2 to achieve the functions of continuous loading and continuous detection is included in the scope of protection of the present invention. In the embodiment, the gas pathogen recovery unit 1 is described by taking a cooling and collecting manner as an example, and its structure comprises a gas inlet 1-1, a cooling module 1-2 and a collector 1-3. In order to facilitate the collection of exhaled gas and improve the continuity of system detection, a disposable mouthpiece can be installed at the position of the gas inlet 1-1 which is the gas inlet of the whole system, and is replaced after each use. A cooling module 1-2 is connected downstream of the gas inlet 1-1 for collecting a sample by negative pressure. Exhaled gas enters the gas pathogen recovery unit 1 from the gas inlet 1-1, and a sample cooled by the cooling module 1-2 is collected by the collector 1-3 and transferred to the pathogen concentration unit 2 via a pipeline. The gas pathogen recovery unit 1 may further comprise a filter 1-4 and a fan 1-5, and expiration other than the sample passes through the filter 1-4 under the action of the fan 1-5 and is output for sterile and non-toxic treatment.

Wherein the pathogen concentration unit 2 comprises an electric concentration device, and the electric concentration device comprises a microchannel, an electrode, and a filter element 2-3. The microchannel comprises a concentration channel 2-1 and a sample channel 2-2, and a filter element 2-3 (the filter element 2-3 can be a semi-permeable membrane, and/or a micro-column array, and/or a gel polymer, and/or a filter element 2-3 of other filter structures with voids) is provided between the concentration channel 2-1 and the sample channel 2-2. The electrode comprises a positive electrode 2-4 and a negative electrode 2-5 (the negative electrode 2-5 can adopt a grounding manner); the positive electrode 2-4 comprises several sub-positive electrodes provided in a spaced array on one side close to the concentration channel 2-1; and the negative electrode is provided on one side close to the sample channel 2-2. In the concentration process, a fluctuating voltage greater than zero in the form of a rectangular wave, and/or a triangular wave, and/or a sine wave, etc. is applied to a single sub-positive electrode, and in the embodiment, the fluctuating voltage is preferably a rectangular wave voltage as shown in FIG. 3, and the voltage of a sub-positive electrode adjacent thereto alternates with the fluctuating voltage, forming a varying potential difference between the adjacent sub-positive electrodes. It should be noted that reference herein to "adjacent" does not refer to physical proximity, but rather refers to the two most adjacent sub-positive electrodes having an alternating voltage relationship, e.g., when one or more of the sub-positive electrodes is grounded, the two adjacent sub-positive electrodes may span one or more of the sub-positive electrodes. The sample flows into the microchannel from the inlet of the microchannel, and under the action of the electrode, pathogens in the sample are regionally enriched on the positive electrode 2-4 side of the concentration channel 2-1, forming a concentrated sample in the concentration channel 2-1. The waste liquid may be harmlessly treated after exiting the sample, for example, a waste reservoir 2-6 may be provided at the outlet of the sample channel 2-2. The electric concentration device can achieve rapid concentration and instant detection of low concentration pathogen samples.

In the embodiment, to further control the flow of sample in the microchannel, a pair of driving electrodes may be provided at the outlet and the inlet of the microchannel. For example, a driving negative electrode is provided at the inlet of the microchannel, and a driving positive electrode is provided at the outlet of the microchannel, so that the sample is subjected to the dual action of the flow field and the electric field in the sample channel 2-2, and the flow field and the electric field together provide the motive force for the pathogenic microorganism particles to flow forward; as another example, a positive drive electrode can be provided at the inlet of the microchannel and a negative drive electrode can be provided at the outlet of the microchannel so that the time of the concentration process can be extended by reducing the rate at which the sample flows in the microchannel.

Figure 2:
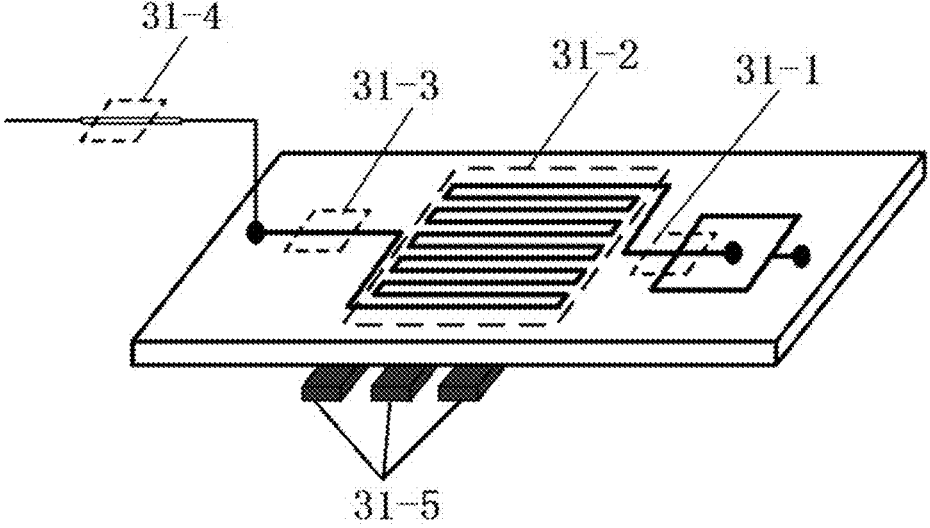
FIG. 2 is a schematic of a microfluidic chip and a temperature control reaction in the embodiment.

In the embodiment, the width of the concentration channel 2-1 is preferably less than the width of the sample channel 2-2; when the concentration of the concentrated sample is more than X times the concentration of the sample before concentration (hereinafter, taking 100 times as an example), assuming that the width $L_1$ of the sample channel 2-2, the width $L_2$ of the concentration channel 2-1, the heights of the two flow channels are H, the flow rate $V_1$ of the sample channel 2-2, the flow rate $V_2$ of the concentration channel 2-1, and M samples existing in the sample channel 2-2 need to be concentrated to the concentration channel 2-1 within T time, then:

Flow: $Q=LHVT$;

Content: $W=M/Q$;

in order that the concentration after concentration is at least 100 times the concentration before concentration, then $W_2 \geq 100W_1$;

then: $M/L_2H_2V_2T \geq 100M/L_1H_1V_1T$;

then: $L_1 V_1/L_2 V_2 \geq 100$.

Wherein the sample detection unit is connected to the concentration channel 2-1, and the sample flows from the outlet of the concentration channel 2-1 to the sample detection unit under the action of a flow field and/or an electric field. The sample detection unit is used for detecting pathogens in the concentrated sample, and the concentrated sample detected by the sample detection unit 3 can be output for harmless treatment. In the embodiment, the sample detection unit 3 preferably comprises a microfluidic amplification module 31 and a fluorescence detection module 32, wherein the microfluidic amplification module 31 comprises a microfluidic channel 31-2, a temperature control module 31-5, an oil storage device and a driving device. The microfluidic channel 31-2 is preferably a zigzag PCR serpentine structure as shown in FIG. 2, the inlets of the microfluidic channel 31-2 are respectively in communication with the concentration channel 2-1 and the oil storage device, and the oil in the oil storage device is driven by the driving device to form a droplet sample in the form of a water-in-oil droplet together with the concentrated sample at the inlet of the microfluidic channel 31-2 (i.e., the droplet generation position 31-1 as shown in FIG. 2). The droplets stay in the reaction region of the microfluidic channel 31-2 and react under the action of the temperature control module 31-5. The temperature control module 31-5 comprises several temperature control monomers provided at intervals to generate a desired temperature change in the main region of the microfluidic channel 31-2, and after the water-in-oil droplet sample is amplified, the amplified pathogen is detected by the detection device.

The fluorescence detection module 32 package may employ an optical detection device, through which analysis and reporting of detection results may be accomplished in cooperation with the computer 4. As shown in FIG. 2, the detection position of the optical detection device may be a chip-type fluorescence detection position 31-3 directly detected on the microfluidic chip, or an off-chip capillary fluorescence detection position 31-4 outside the microfluidic chip.

In the embodiment, detection is preferably performed using a fluorescence detection method, in which a droplet containing a pathogen is first subjected to an amplification reaction to generate fluorescence. The generation of a fluorescent signal by an amplification reaction in a droplet can be achieved in several methods:

1, Taqman Probe Fluorescence Quantitative PCR Method

In this method, the primer design preferably comprises the following steps: according to the hemagglutinin gene sequence of avian influenza virus H9 subtype of AIV in Gen Bank, the homology analysis was performed by DNAMAN software, and specific primers and Taq Man fluorescent probe were designed in the conservative region by Primer Express5.0 software. The TaqMan fluorescent probe labels a reporter fluorophore such as FAM, JOE, cy5, ROX, etc. and a quencher fluorophore preferably BHQ1 and BHQ2. The primer and probe sequences are: probe 5 'FAM-ctcaccattt-attcgactgtcgcctc-BHQ1 3', upstream primer: 5'ccaattcg-gaacgggacct 3' and downstream primers: 5'acag-gaaggcagcaaacc 3'. The reaction system for fluorescent quantitative PCR amplification uses the Taq enzyme reaction system. The reaction conditions for fluorescent quantitative PCR amplification are: denature 5 min at 95° C.; fluorescence detection was performed at 55° C. for 40 cycles of 95° C. for 5s and 55° C. for 20s.

2. RT-PCR Fluorescent Dye Rapid Detection Method

In this method, RT-PCR fluorochrome is used for rapid detection of H9N2 subtype avian influenza virus. The fluorochrome used is SYBR Green I, and other fluorochromes are not limited. The enriched virus particles were extracted by Trizol method for RNA, and then the HA gene of H9N2 subtype influenza virus was detected by RT-PCR fluorescent dye method using RNA as template. Primers were designed as F:5'cctcaccatttattcgactgt 3' and R:5'ayccattgracatggcccag 3'. The fluorescent RT-PCR method was established by adding SYBR Green I fluorescent dye to the PCR reaction system. The reaction conditions were 40 cycles at 42° C. for 5 min, at 95° C. for 10s, at 95° C. for 5s, and at 60° C. for 34s.

3. LAMP Detection Method

In this method, H9N2 subtype avian influenza virus was enriched, extracted by RNA, reverse transcribed into cDNA, and detected by loop-mediated isothermal amplification (LAMP) reaction system. Primers were designed for H9N2 subtype avian influenza virus as follows:

FIP 5' cgttgttctttgagtcaaccatc-acaagcaaagcatgttcag 3'
BIP 5'agacgcccaatacacaaataataga-gtctgcgcagtatcagtg 3'

F3 5' ggaatgtgcttacagtgga 3'
B3 5'tgtcaatccttgtgtacagat 3'

The reaction conditions are reactions at constant temperature 60° C.-65° C. for 30-90 min. SYBR Green I dye was added during the amplification of the LAMP method to demonstrate the presence of pathogens based on the presence or absence of fluorescence in the droplet.

Figure 4:
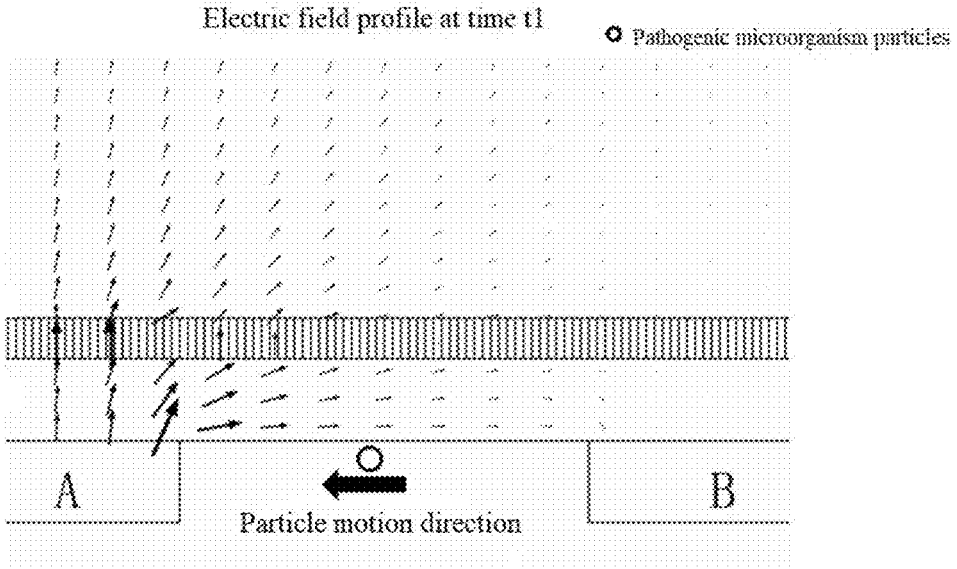
FIG. 4 is a graph of the electric field distribution at time t1 in FIG. 3.
Figure 5:
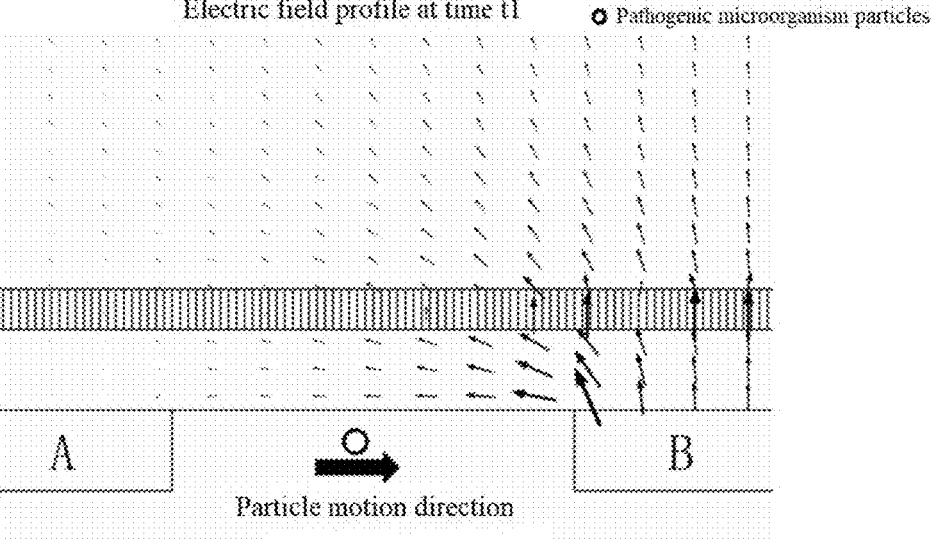
FIG. 5 is a graph of the electric field distribution at time t2 in FIG. 3.
Figure 6:
FIG. 6 is a graph showing the enrichment state of pathogen particles between the neutron positive electrode A and the sub-positive electrode B in FIG. 3.

This embodiment also provides an automatic pathogen-from-expiration detection method using the above-described automatic pathogen-from-expiration detection system. The method comprises:

S1, making the sample recovered by the gas pathogen recovery unit 1 enter the pathogen concentration unit 2;
S2, concentrating the condensate sample;
S2-1, under the action of the positive electrode 2-4 and the negative electrode 2-5, gradually biasing the pathogen particles to one side of the positive electrode 2-4, making the pathogen particles enter the concentration channel 2-1 via the filter element, and making the waste liquid enter the sample channel 2-2;
S2-2, as shown in FIG. 3, applying a fluctuating voltage greater than zero to a single sub-positive electrode, and alternating the voltage of the sub-positive electrode adjacent thereto with the fluctuating voltage to form a varying potential difference between the adjacent sub-positive electrodes. Note that a plurality of sub-positive electrodes may be provided, and when the plurality of sub-positive electrodes is provided, the positive electrodes include a plurality of groups of adjacent sub-positive electrodes, and only one group (i.e., adjacent sub-positive electrodes A and B) is exemplified in FIG. 3. Here, the electric field distribution at time t1 is shown in FIG. 4, and the electric field distribution at time t2 is shown in FIG. 5. The pathogen particles reciprocate between the adjacent two sub-positive electrodes and gradually accumulate in the middle region of the adjacent two sub-positive electrodes, and the zone enrichment state formed under the control of multiple sub-positive electrodes is as shown in FIG. 6; there can be several enrichment regions in which pathogen particles are accumulated formed by this step, and a few or even one enrichment region can be formed by adjusting the operation or not of the electrodes, so that the pathogen in the expiration can be effectively concentrated, which not only greatly reduces the expiration required to be collected by the gas collection and condensation unit, but also increases the probability that the pathogen in the concentrated sample can be detected, so that the convenience and accuracy of detection can be greatly improved; only a small amount of concentrated sample can be sent to the sample detection unit 3 for detection to facilitate the miniaturization of the system and the continuity of detection;

In the embodiment, the preferable control method of this step is: providing a plurality of individual sub-positive electrodes, wherein a fluctuating electric field is formed among a number of sub-positive electrodes therein, forming one or more enrichment regions, and the number of electrodes supplying voltage during enrichment can also be gradually reduced to form fewer enrichment regions for further enrichment.

The following is illustrated as a preferred scheme (assuming that N single sub-positive electrodes are provided, numbered sequentially 1, 2, 3, 4 . . . , N):

firstly, applying a fluctuating voltage greater than zero on the first, third, fifth, sub-positive electrodes, applying an alternating voltage with an alternating change trend with the fluctuating voltage on the second, fourth, sixth, . . . sub-positive electrodes, until pathogen particles are enriched between the first and second sub-positive electrodes, between the second and third sub-positive electrodes, and between the third and fourth sub-positive electrodes . . . , forming A enrichment regions;

then, controlling the second, fourth, sixth, . . . sub-positive electrodes to be grounded, applying a fluctuating voltage greater than zero on the first, fifth, ninth, . . . sub-positive electrodes, and applying an alternating voltage having an alternating change trend with the fluctuating voltage on the third, seventh, eleventh, . . . sub-positive electrodes, until pathogen particles are enriched between the first and third sub-positive electrodes, between the third and fifth sub-positive electrodes, and between the fifth and seventh sub-positive electrodes . . . , forming B enrichment regions of which the number is less than A;

then, the third, the seventh, the eleventh, . . . sub-positive electrodes are further controlled to be grounded, a fluctuating voltage greater than zero is applied to the first, the ninth, the seventeenth, sub-positive electrodes, and an alternating voltage with an alternating variation trend with the fluctuating voltage is applied to the fifth, the thirteen, the twenty-first, . . . sub-positive electrodes until pathogen particles are enriched between the first and the fifth sub-positive electrodes, between the fifth and the ninth sub-positive electrodes, and between the ninth and the thirteen sub-positive electrodes . . . forming C enrichment regions of which the number is less than B; by so doing, the pathogen particle enrichment region is gradually reduced, while the amount of pathogen particles concentrated in each enrichment region is gradually increased.

S2-3, controlling the positive electrode 2-4 to be grounded, and transporting the concentrated sample to the sample detection unit 3; and S3, immediately detecting the concentrated sample in the sample detection unit 3. This preferred control method allows for orderly concentration of pathogen particles into concentrated samples of desired concentration.

The above description is of preferred embodiments of the invention and is not intended to limit the invention. It will be understood by a person skilled in the art that various changes in form and details may be made therein without departing from the spirit and scope of the invention.

The invention claimed is:

1. An automatic pathogen-from-expiration detection system, comprising:

a gas pathogen recovery unit;

a pathogen concentration unit; and a sample detection unit, wherein the gas pathogen recovery unit and the pathogen concentration unit are coupled to realize continuous loading and continuous detection;

the pathogen concentration unit comprises:

a microchannel;

an electrode; and a filter element, the microchannel comprises:

a concentration channel; and a sample channel, wherein a filter element is provided between the concentration channel and the sample channel;

the electrode comprises: a positive electrode; and a negative electrode, the positive electrode comprises several sub-positive electrodes provided in a spaced array on one side close to the concentration channel, and the negative electrode is provided on one side close to the sample channel; a fluctuating voltage greater than zero is applied to a single sub-positive electrode, and the voltage of the sub-positive electrode adjacent thereto alternates with the fluctuating voltage, so that a varying potential difference is formed between the adjacent sub-positive electrodes; fa sample formed in the gas pathogen recovery unit flows into the microchannel, and under the action of the electrode, the pathogens in the sample are regionally enriched on the positive electrode side of the concentration channel to form a concentrated sample in the concentration channel; and the sample detection unit is connected to the concentration channel for detecting pathogens in the concentrated sample.

2. The automatic pathogen-from-expiration detection system according to claim 1, characterized by further comprising a first driving device, the sample being driven into the microchannel by the first driving device.

3. The automatic pathogen-from-expiration detection system according to claim 2, characterized in that the first driving device comprises a positive pressure pump, and/or a negative pressure pump, and/or a syringe pump, and/or a peristaltic pump.

4. The automatic pathogen-from-expiration detection system according to claim 1, characterized in that a pair of driving electrodes are provided at an outlet and an inlet of the microchannel.

5. The automatic pathogen-from-expiration detection system according to claim 1, characterized in that the sample detection unit comprises a microfluidic channel, a temperature control module, a detection device, an oil storage device and a second driving device, inlets of the microfluidic channel are respectively in communication with the concentration channel and the oil storage device, the oil in the oil storage device is driven by the second driving device to form a water-in-oil droplet sample together with the concentrated sample at the inlet of the microfluidic channel, the temperature control module comprises several temperature control monomers to generate a required temperature change in the main region of the microfluidic channel, the water-in-oil droplet sample is amplified, and the amplified pathogen is detected by the detection device.

6. The automatic pathogen-from-expiration detection system according to claim 1, characterized in that the fluctuation form of the fluctuating voltage greater than zero comprises a rectangular wave, and/or a triangular wave, and/or a sinusoidal wave.

7. The automatic pathogen-from-expiration detection system according to claim 1, characterized in that the filter element is a semi-permeable membrane, and/or an array of micro-columns, and/or a gel polymer, and is a filter structure with voids.

8. The automatic pathogen-from-expiration detection system according to claim 1, characterized in that the concentration channel has a width smaller than that of the sample channel.

9. The automatic pathogen-from-expiration detection system according to claim 8, characterized in that the width $L_1$ of the sample channel and the width $L_2$ of the concentration channel satisfy:

$$L_1 V_1 / L_2 V_2 \geq X$$

13

14 wherein $V_1$ is a flow rate of the sample channel, $V_2$ is a flow rate of the concentration channel, and X is a ratio of the concentration of the concentrated sample to the concentration of the sample before concentration.

10. An automatic pathogen-from-expiration detection method, comprising:

making a sample recovered by a gas pathogen recovery unit enter the pathogen concentration unit;

under the action of a positive electrode and a negative electrode, gradually biasing pathogen particles to one side of the positive electrode, and making the pathogen particles enter the concentration channel through the filter element; applying a fluctuating voltage greater than zero on a single sub-positive electrode, wherein the voltage of the sub-positive electrode adjacent thereto alternates with the fluctuating voltage, forming a varying potential difference between the adjacent sub-positive electrodes, and the pathogen particles reciprocate between the two adjacent sub-positive electrodes and gradually enrich in the middle region of the two adjacent sub-positive electrodes; and driving the concentrated sample to move to the sample detection unit; and immediately detecting the concentrated sample in the sample detection unit.

11. The automatic pathogen-from-expiration detection method according to claim 10, characterized in that several sub-positive electrodes are provided, wherein some or all the single sub-positive electrodes are applied with a fluctuating voltage, and a fluctuating electric field is formed among a number of sub-positive electrodes therein, forming one or more enrichment regions, and the number of electrodes supplying voltage during enrichment can also be gradually reduced to form fewer enrichment regions for further enrichment.

* * * * *